US 6,719,998 B1

(12) United States Patent
Golomb et al.

(10) Patent No.: US 6,719,998 B1
(45) Date of Patent: Apr. 13, 2004

(54) TREATMENT OF RESTENOSIS (75) Inventors: Gerson Golomb, Efrat (IL); Haim Danenberg, Jerusalem (IL)

(73) Assignees: Yissum Research Development Company of the Hebrew University of Jerusalem, Jerusalem (IL); Hadasit Medial Research Services and Development Ltd., Jerusalem (IL)

( * ) Notice: Subject to any disclaimer, the term of this patent is extended or adjusted under 35 U.S.C. 154(b) by 0 days.

(21) Appl. No.: 09/743,705

(22) PCT Filed: Jul. 14, 1999

(86) PCT No.: PCT/IL99/00387
§ 371 (c)(1),
(2), (4) Date: Mar. 22, 2001

(87) PCT Pub. No.: WO00/03677
PCT Pub. Date: Jan. 27, 2000

(30) Foreign Application Priority Data

Jul. 14, 1998 (IL) .................................................. 125336

(51) Int. Cl.[7] .......................... A61K 9/127; A61K 9/14; A01N 57/00
(52) U.S. Cl. ...................... 424/450; 424/400; 424/489; 514/75; 514/102
(58) Field of Search ................................. 424/450, 489, 424/490; 514/75, 102, 824

(56) References Cited

U.S. PATENT DOCUMENTS

| 4,067,971 | A |   | 1/1978  | Francis et al. |
| 4,216,211 | A |   | 8/1980  | Francis |
| 5,096,717 | A |   | 3/1992  | Wirth et al. |
| 5,196,409 | A |   | 3/1993  | Breuer et al. |
| 5,312,954 | A |   | 5/1994  | Breuer et al. |
| 5,338,731 | A |   | 8/1994  | Breuer et al. |
| 5,492,926 | A | * | 2/1996  | Cullinan et al. ............ 514/422 |
| 5,652,227 | A |   | 7/1997  | Teronen et al. |
| 5,733,564 | A |   | 3/1998  | Lehtinen |
| 5,741,514 | A | * | 4/1998  | Barenholz et al. .......... 424/450 |
| 5,760,030 | A |   | 6/1998  | Bryant et al. ............... 514/213 |
| 5,792,885 | A |   | 8/1998  | Ham et al. |
| 5,882,656 | A |   | 3/1999  | Bechard et al. |
| 5,932,563 | A |   | 8/1999  | Stokes et al. |
| 5,932,580 | A |   | 8/1999  | Levitzki et al. |
| 5,994,341 | A |   | 11/1999 | Hunter et al. |

FOREIGN PATENT DOCUMENTS

| EP | 0459 318    |   | 12/1991 |
| WO | WO 97/43437 | * | 11/1997 |
| WO | WO 88 00289 |   | 2/1998  |
| WO | PCT 00 21540|   | 10/1999 |
| WO | PCT 00 34293|   | 6/2000  |
| WO | WO 00/64516 |   | 11/2000 |

OTHER PUBLICATIONS

Monkkonen et al (Calcif Tissue Int., vol. 35, 1995).*
PCT Search Report.

(List continued on next page.)

Primary Examiner—Michael G. Hartley
(74) Attorney, Agent, or Firm—Morgan & Finnegan L.L.P.; Christopher A. Hughes, Esq.

(57) ABSTRACT

Bisphosphonate (BP), pyrophosphate (PP) a complex of BP or PP, a polymer of BP or PP or pharmaceutically acceptable salt or ester thereof, are used for the prevention or treatment of vascular restenosis.

6 Claims, 1 Drawing Sheet

OTHER PUBLICATIONS

Van Rooijen, N., Kors, N., Ter Hart, H. amd Claassen, E., 1988. *In vitro and in vivo elimination of macrophage tumor cells using liposome–encapsulated dichloromethylene diphosphonate. Virchows Arch. B (Cell Pathol.).* 54: 241–245.

Van Rooijrn, N., Claassen, E., 1988, *In vivo elimination of macrophages in spleen andliver, using liposome encapsulated drugs: methods and applications. In: Liposomes as drug carriers: Trends and progress.* Ed. G. Gregoriadis. John Wiley and sons, Chichester, U.K. (chapter 9) pp. 131–143.

Thepen, T., Van Rooijen, N., and Kraal, G., 1989. *Alveolar macrophage elimination in vivo is associated with an increase in pulmonary immune response in mice. J. Exp. Med.* 170: 499–509.

Monkkonen, J., Van Rooijen, N. and Ylitalo, P., 1991. *Effects of clodronate and pamidronate on splenic and hepatic phagocytic cells of mice. Pharmacol. Toxicol.* 68: 284–286.

Van Rooijen, N., 1992. *Liposomes as an vivo tool to study and manipulate macrophage function: Introduction 41st Forum in Immunology. Res. Immunol.* 143: 177–178.

Van Lent, P.L.E.M., Van De Hoek, A., Van Den Bersselaar, L., Spanjaards, M.F.R., Van Rooijen, N., Dijkstra, C.D., Van De Putte, L.B.A. and Van Den Berg, W.B., 1993. *In vivo role of phagocytic synovial lining cells in onset of experimental arthritis. Am. J. Pathol.* 143: 1226–1237.

Biewenga, et al., 1995. *Macrophage depletion in the rat after intraperitoneal administration of liposome–encapsulated clodronate: depletion kinetics and accelerated repopulation of peritoneal and omental macrophages by administration of Freund's adjuvnat. Cell Tissue Res.* 280: 189–196.

Gaytan, F., Belliso, C., Morales, C., Garica, M., Van Rooijen, N. and Aguilar, E., 1996. *In vivo manipulation (depetion versus activation) of testicular macrophages: central and local effects. J. Endocrinol.* 150: 57–65.

Van Rooijen, N., Bakker, J., Sanders, A., 1997, *Transient suppression of macrophage functions by liposome–encapsulated drugs. Trends in Biotechnology*, 15(5): 178–185.

Van Rooijen, N., Kros, N. Kraal, G., 1989. *Macrophage subset repopulation in the spleen: differential kinetics after lipsome–mediated elimination. J. Leuk. Biol.* 45: 97–104.

Van Rooijen, N., 1992. *Macrophages as accessory cells in the in vivo humoral immune response: from processing of particulate antigens to .regulation by suppression. Semin. Immunol.* 4: 237–245.

Rogers, C., Welt, F., Karnovsky, M and Edelman, E., 1996. *Monocyte Recruitment and Neointimal Hyperplasia in Rabbits. Arteriosclerosis, Thrombosis, and Vascular Biology.* 16:1312–1318.

www.clodronateliposomes.com, copyright (c) 1984–2003, download date Sep. 4, 2003.

Abstract, Kunitomo et al., "Experimental Induction of Athero Sclerosis in Guinea–Pigs Fed a Cholesterol Vitamin D–2–Rich Diet", (1983).

Mökkönen et al., "The Effect of Liposome–Encapsulated and free Clodronate on the Growth of Macrophage–like Cells *In Vitro:* The Role of Calcium and Iron", *Calcif Tissue International*, (1993), vol. 53, pp. 139–146.

Gennaro, "Parenteral Preparations", *Remington: The Science and Practice of Pharmacy*, $20^{th}$ Edition, Chapter 41, pp. 780–920.

Kramsch et al., "Th effect of Agents Interfering with Soft Tissue Calcification and Cell Proliferation on Calcific Fibrous–Fatty Plaques in Rabbits", *Circulation Research*, (1978), vol. 42, No. 4, pp. 562–570.

Mönkkönen et al., "Growth Inhibitions of Macrophage–Like and Other Cell Types by Liposome–Encapsulated, Calcium––Bound, and Free Bisphosphonates *In Vivo*", *Journal of Drug Targeting*, (1994), vol. 2, pp. 299–308.

Fleisch, "Bisphosphonates in bone disease", *Parthenon Publishing Group Inc.*, (1997), pp. 184–210.

Mak et al., "Clinical Trials to prevent Restenosis after Precutaneous Coronary Revescularization", *The NY Academy of Sciences*, (1994), pp. 225–277.

Leclerc et al., "Drug prevention of restenosis after angioplasty: an update", *Elsevier Science*, (1995), pp. 722–724.

Lefkovits et al., "Pharmacological Approaches for the Prevention of Restenosis After Percutaneous Coronary Intervention", *Progress in Cardiovascular Disease*, (1997), vol. 40, No. 2, pp. 141–158.

Hamon et al., "Restenosis after coronary angioplasty", *European Heat Journal*, (1995), vol. 16, pp. 33–48.

Gottsauner–Wolf et al., "Influence of local delivery of the protein tyrosine kinase receptor inhibitor tyrphostin–47 on smooth–muscle cell proliferation in a rat carotid balloon––injury model", *American Heart Journal*, (1996), vol. 19, pp. 347–356.

Donbrow, "Microcapsules and Nanoparticles in Medicine and Pharmacy", CRC Press, Boca Raton, Fl. pp. 347.

Shioi et al., "β–Glycerophoshate Accelerates Calcification in Cultured Bovine Vascular Smooth Muscle Cells", *Arteriosclerosis, Thrombosis and Vascular Biology*, (1995), vol. 15, No. 11, pp. 2003–2009.

Paspaliaris et al., "Clodronate Inhibits Contraction and prevents the Action of L–Type Calcium Channel Antagonists in Vascular Smooth Muscle", (1991), *Journal of Bone Mineral Research*, vol. 6, No. 8, pp. 835–841.

Bellah et al., "Idiopathic arterial calcification of infancy: Prenatal an postnatal effects of therapy in an infant", (1992), *The Journal of Pediatrics*, vol. 121, No. 6, pp. 930–933.

Waller et al., "Coronary Artery and Saphenous Vein Graft Remodeling: A Review of Histologic Findings after Various Interventional Procedure—Part VI", *Clin. Cardiol.*, (1997), vol. 20, pp. 153–160.

Anderson et al., "A review of randomized trials comparing coronary angioplasty and bypass grafting", *Curr–Opin–Cardiol*, (1996), vol. 11, No. 6, pp. 583–590.

Moorman et al., "Percutaneous Transluminal Coronary Angioplasty (PTCA): Long–term Outcome and Aeromedical Implications", *Aviation, Space and Environmental Medicine*, (1996), vol. 67, No. 10, pp. 990–996.

Laurent et al., "The arterial wall: a new pharmacological and therapeutic target", *Fundam Clin Pharmacol*, (1996), vol. 10, pp. 243–257.

Schwartz, "The vessel wall reaction in restenosis", *Semin–Interv–Cardiol*, (1997), vol. 2, pp. 83–88.

Allaire et al, "Endothelial Cell Injury in Cardiovascular Surgery: The Intimal Hyperplastic Response", *Ann Thorac Surg*, (1997), vol. 63, pp. 582–591.

Webb et al, "Inhibition of Bioprosthetic Heart Valve Calcification with Aminodiphosphonate Covalently Bound to Residual Aldehyde Groups", *Ann Thorac Surg.*, (1988), vol. 46, pp. 309–316.

Wagner et al., "Contrasting Effects of Ethane–1–Hydroxy–1, 1–Diphosphonate (EHDP) on the Refression of two types of Dietary–Induced Atherosclerosis", *Atherosclerosis*, (1977), vol. 27, pp. 419–435.

Daoud et al., "The effect of ethane–1–hydroxy–1, 1–diphosphonate (EHDP) on necrosis of atherosclerotic lesions", *Atherosclerosis*, (1987), vol. 67, pp. 41–48.

Walsh et al., "Molecular strategies to inhibit restenosis: modulation of the vascular myocyte phenotype", *Semin Intervent Cardiol*, (1996), vol. 1, pp. 173–179.

Hermann et al., "Pharmacological Approaches to the prevention of Restenosis Following Angioplasty", *DRUG*, (1993), vol. 46, No. 1, pp. 18–52.

Rubin et al.,"Cellular and Molecular Mechanisims of Radiation Inhibition of Restenosis. Part I: Role of the Macrophage and Platelet–Derived Growth Factor", *Int. J. Radiation Oncology Biol. Phys.* (1998), vol. 40, pp. 929–941.

Monkkonen et al., "Studies on Liposome Formulations for Intra–articular Delivery of Clodronate", *Journal of Controlled Release*, (1995), vol. 35, pp. 145–154.

* cited by examiner

TREATMENT OF RESTENOSIS

The present application is the national stage under 35 U.S.C. 371 of PCT/IL99/00387, filed Jul. 14, 1999.

FIELD OF THE INVENTION

The present invention is concerned with compositions capable of preventing, inhibiting or reducing restenosis (sometimes referred to in the art as "accelerated arteriosclerosis" and "post-angioplasty narrowing").

PRIOR ART

The following references are considered to be pertinent for the purpose of understanding the background of the present invention.
1. Waller, B. F., Orr, C. M, VanTassel J., et al. *Clin-Cardiol.* 20(2):153–60, (1997).
2. Anderson, W. D, King, S. Br., *Curr-Opin-Cardiol.*, 11(6): 583–90, (1996).
3. Moorman, D. L., Kruyer, W. B., Jackson, W. G., *Aviat-Space-Environ-Med.* 67(10):990–6, (1996).
4. Laurent S, Vanhoutte P, Cavero I, et al., *Fundam. Clin. Pharmacol.*, 10(3):243–57, (1996).
5. Walsh, K., Perlman, *Semin-Interv-Cardiol.*, 1(3):173–9, (1996).
6. Schwartz, R. S., *Semin-Interv-Cardiol.*, 2(2):83–8, (1997).
7. Allaire, E, Clowes, A. W. *Ann. Thorac. Surg.*, 63:582–591, (1997).
8. Hamon. M., Bauters, C., McFadden, E. P, et al., *Eur. Heart J.*, 16:33s-48s, (1995).
9. Gottsauner-Wolf, M., Moliterno, D. J, Lincoff, A. M., Topol, E. J., *Clin. Cardiol.*, 19:347–356, (1996).
10. Herrman, J. P. R., Herrnans, W. R. M., Vos, J., Serruys, P. W., *Drugs*, 46:18–52, (1993).
11. Leclerc, G., Voisine, P., Bouchard, M., Fleser, A., Martel, R. *Elsevier Science*, 722–724, (1995).
12. Topol, E., *The NY Academy of Sciences*, 225–277, (1997).
13. Fleisch, H., in: Bisphosphonates in bone disease. Parthenon Publishing Group Inc., pp. 184–186 (1997).
14. Mönkkönen, J., Taskinen, M., Auriola, S., Urtti, *J. Drug Target*, 2:299–308, (1994).
15. Kramsche, D. M., and Chan, C. T., *Circ. Res.*, 42:562–572, (1978).
16. Braunwald, E. *Heart Disease* in: A textbook of cardiovascular medicine; 5th Ed., W. B. Saunders Company: Philadelphia, (1997).
17. Gennaro Alfonso, R. Remington, in: The Science and Practice of Pharmacy, Mack Publishing, Easton Pa., 19th ed., (1995).
18. Mönkkönen, J., and Heath, T. D., *Calcif. Tissue Int.*, 53:139–145, (1993).
19. M. Donbrow in: Microencapsulation and Nanoparticles in Medicine and Pharmacy, CRC Press, Boca Raton, Fla., p. 347.

The above references will be acknowledged in the text below by indicating their number (as shown in brackets) from the above list.

BACKGROUND OF THE INVENTION

Over the past decade, mechanical means of achieving revascularization of obstructive atherosclerotic vessels have been greatly improved. Percutaneous transluminal coronary angioplasty (PTCA) procedures include, but are not limited to, balloon dilatation, excisional atherectomy, endoluminal stenting, rotablation, and laser ablation. However, revascularization induces thrombosis and neointimal hyperplasia, which in turn cause restenosis in a substantial proportion of coronary arteries after successful balloon angioplasty and in aortacoronary saphenous vein bypass graft and other coronary grafts. Furthermore, intimal hyperplasia causes restenosis in many superficial femoral angioplasties, carotid endarterectomies, and femoro-distal vein bypasses. The introduction of endovascular stents has contributed to reduce the incidence of restenosis, but this problem still remains significant[1-9]. Despite extensive research on the incidence, timing, mechanisms and pharmacological interventions in humans and animal models, to date no therapy exists which consistently prevents coronary restenosis[10-12]. Compositions and methods for the reduction or prevention of restenosis are still today greatly desired.

Bisphosphonates (BP) (formerly called diphosphonates) are compounds characterized by two C-P bonds. If the two bonds are located on the same carbon atom (P-C-P) they are termed geminal bisphosphonates. The BPs are analogs of the endogenous inorganic pyrophosphate which is involved in the regulation of bone formation and resorption. The term bisphosphonates is generally used for geminal and non-geminal bisphosphonates. The BPs and pyrophosphates may at times form together polymeric chains. BPs act on bone because of their affinity for bone mineral and are potent inhibitors of bone resorption and ectopic calcification. BPs or pyrophosphate have been used clinically mainly as (a) antiosteolytic agents in patients with increased bone destruction, especially Paget's disease, tumor bone disease and osteoporosis; (b) skeletal markers for diagnostic purposes (linked to $^{99m}$Tc); (c) inhibitors of calcification in patients with ectopic calcification and ossification, and (d) antitartar agents added to toothpaste[13].

SUMMARY OF THE INVENTION

In accordance with the present invention, a BP or pyrophosphate (collectively herein: "active ingredient") is used for the treatment or prevention of vascular restenosis. The term bisphosphonate (BP) as used herein denotes both geminal and non-geminal bisphosphonates. The term "active ingredient" encompasses in its scope also polymeric chains of the BPs or pyrophosphate, particularly such chains consisting of up to 40 BP monomers. Preferred active ingredients are compounds of the following formula (I):

wherein R represents O or a $CR_1R_2$ group;
 $R_1$ is H, OH or a halogen group; and
 $R_2$ is halogen; linear or branched $C_1$–$C_{10}$ alkyl or $C_2$–$C_{10}$ alkenyl optionally substituted by heteroaryl or heterocyclyl $C_1$–$C_{10}$ alkylamino or $C_3$–$C_8$ cycloalkylamino where the amino may be a primary, secondary or tertiary; —NHY where Y is hydrogen, Cs–Cg cycloalkyi, aryl or heteroaryl; or $R_2$ is —SZ where Z is chlorosubstituted phenyl or pyridinyl.

The present invention thus provides the use of said active ingredient, a complex of said active ingredient or a pharmaceutically acceptable salt or ester thereof, for the preparation of a medicament for the prevention or treatment of vascular restenosis.

The present invention also provides a method of treatment of restenosis, comprising administering to an individual in need thereof an effective amount of said active ingredient, a complex thereof or a pharmaceutically acceptable salt or ester thereof.

The present invention still further provides a pharmaceutical composition for the prevention or treatment of restenosis, comprising as an active ingredient, an effective amount of said active ingredient, a pharmaceutically acceptable free acid, a complex or a salt thereof, optionally together with a pharmaceutically acceptable carrier or diluent. A particularly preferred carrier is a liposome preparation.

The term "effective amount" means to denote an amount of the active ingredient which is effective in achieving the desired therapeutic result, namely prevention or reduction of vascular restenosis. The effective amount may depend on a number of factors including: weight and gender of the treated individual; the type of medical procedure, e.g. whether the vascular restenosis to be inhibited is following balloon angioplasty, balloon angioplasty followed by deployment of a stent, etc.; the mode of administration of the active ingredient (namely whether it is administered systemically or directly to the site); the type of carrier being used (e.g. whether it is a carrier that rapidly releases the active ingredient or a carrier that releases it over a period of time); the therapeutic regime (e.g. whether the active ingredient is administered once daily, several times a day or once every few days); clinical factors influencing the rate of development of restenosis such as diabetes, smoking, hypercholesterolemia, renal diseases, etc.; anatomical factors such as whether there is severe preangioplasty stenosis, total occlusion, left anterior descending coronary artery location, saphenous vein graft lesion, long lesions, multivessel or multilesion PTCA; on the dosage form of the composition; etc. Moreover, procedural variables may also have bearing on the dosage such as greater residual stenosis following PTCA, severe dissection, intimal tear, appropriate size of balloon, and the presence of thrombus. The artisan, by routine type experimentation should have no substantial difficulties in determining the effective amount in each case.

The invention is applicable for the prevention, reduction or treatment of vascular restenosis and mainly, but not limited to, coronary restenois after angioplasty. Vascular restenosis results from various angioplasty procedures including balloon angioplasty, intravascular stent implantation or other methods of percutaneous angioplasty (including angioplasty of coronary arteries, carotid arteries, and other vessels amenable for angioplasty) as well as for restenosis resulting from vascular graft stenosis (e.g., following by-pass surgery)[16]. In addition, the invention is also applicable for the prevention, reduction or treatment of vascular resteriosis in peripheral arteries and veins.

One exemplary application of the invention is to prevent and treat in-stent restenosis. It is a widely acceptable medical procedure to deploy a stent within a blood vessel within the framework an angioplastic procedure, to support the walls of the blood vessel. However, very often restenosis occurs notwithstanding the presence of the stent within the blood vessel. In accordance with the invention the above noted active ingredient may be administered, either systemically or directly to the site, in order to prevent or inhibit such restenosis. Potentially said active ingredient may be formulated in a manner allowing its incorporation onto the stent which will in fact yield administration of said active ingredient directly at the site. The active ingredient may be formulated in that manner, for example, by including it within a coating of the stent. Examples of coating are polymer coatings, e.g., made of polyurethane, or a gel.

The active ingredient used in accordance with the invention may be formulated into pharmaceutical compositions by any of the conventional techniques known in the art (see, for example, Alfonso el al., 1995[17]). The compositions may be prepared in various forms such as, capsules, tablets, aerosols, solutions, suspensions, or as a coating of a medical device such as a stent (see above), etc. In addition, the pharmaceutical compositions of the invention may be formulated in a form suitable for topical administration with a carrier or in a delivery form permitting penetration of the active ingredient through the skin and into the body in order to act systemically. The preferred administration form in each case will depend on the desired delivery mode, which is usually that which is the most physiologically compatible in accordance with the patient's condition, other therapeutic treatments which the patient receives, etc. In accordance with a preferred embodiment of the invention, said active ingredient is formulated into a particulate form. This may be achieved by encapsulating or impregnating the active ingredient into particles, e.g., polymeric particles, lipid vesicles, or liposomes. Furthermore, such particles may be particles of polymerized active ingredient (see below). Particularly preferred are liposomal preparations of said active ingredient. The liposomes may be prepared by any of the methods known in the art (regarding liposome preparation methods see Mönkkönen et al., 1994[14] and Mönkkönen et al., [18]). The liposomes may be positively charged, neutral or negatively charged (negatively charged liposomes being currently preferred), and may be single or multilamellar. At times, compositions comprising a combination of free active ingredient (i.e. non-encapsulated) and said active ingredient encapsulated within liposomes may also be used.

By a preferred embodiment of the invention, the active ingredient is preferably selected from the group of such compounds which are capable of undergoing intracellular metabolism. One preferred active ingredient for this group is the compound clodronate[13] having the following formula (II):

(II)

Clodronate, was previously described for use in the treatment of hypercalcemia resulting from malignancy in the treatment of tumor associated osteolysis[13], and as an inhibitor of macrophages[14, 18].

Other preferred active ingredients of this group are Etidronate and Tiludronate having the following formulae (III) and (UV) respectively:

(III)

(IV)

Additional BPs having activities similar to that of clodronate are also preferred in accordance with the invention. Such BPs may be selected on the basis of their ability to mimic biological activity of clodronate. This includes, for example: in vitro activity in inhibiting phagocytic activity of phagocytic cells, e.g., macrophages and fibroblasts; inhibi- tion of secretion of IL-1 and/or IL-6 and/or TNF-α from macrophages; in vivo activity, e.g., the ability of the tested BP to prevent or reduce restenosis in an experimental animal model such as, for example, the rat or rabbit carotid catheter injury model described in Example 1 below, or porcine model of restenosis; etc.

Another preferred group of active ingredients in accordance with the invention are the amino-BPs and any other nitrogen-containing BPs having the following general formula (V):

(V)

wherein x represents $C_1$–$C_{10}$ alkylamino or $C_3$–$C_8$ cycloalkylamino, where the amino may be primary, secondary or tertiary; or x represents NHY where Y is hydrogen, $C_3$–$C_8$ cycloalkyl, aryl or heteroaryl The BPs belonging to this group are believed not to be metabolized and have been shown at relatively low concentrations to induce secretion of the interleukin IL-1 and cause, at relatively high concentrations, apoptosis in macrophages[18]. Preferred BPs belonging to this group are for example, Pamidronate and Alendronate having the following formulae (VI) and (VII), respectively.

(VI)

(VII)

Although the geminal BPs are preferred BPs in accordance with the invention, non-geminal BPs, monophosphonates of BPs termed generally as phosphonates may also be used as active ingredients in accordance with the invention.

Another preferred active ingredient is pyrophosphate having the formula (VIII):

(VIII)

Pyrophosphate is preferably formulated and administered in a liposome or a polymeric particle preparation.

The composition of the invention may comprise said active ingredient either in their free acid form, complexed with metal cations such as calcium, magnesium or organic bases or may be in the form of salts or esters or they may be polymerized to yield polymers of up to 40 monomers. The salts may be sodium, potassium, ammonium or calcium salts or salts formed with any other suitable basic cation (e.g. organic amino compounds). The salts or polymers may be in a micronized particulate form having a diameter within the range of about 0.01–10 μm, preferably within a range of about 0.1–5 μm. The active ingredients in the compositions of the invention being either in their free acid form or salt form may be with or without water of crystallization (hydrous and anhydrous).

By a preferred embodiment, the active ingredient is encapsulated within a liposome prepared by any of the methods known in the art. Suitable liposomes in accordance with the invention are preferably non toxic liposomes such as, for example, those prepared from phosphatidylcholine phosphatidylglycerol, and cholesterol, e.g., as described below. In many cases, use of the active ingredient encapsulated in a liposome results in enhanced uptake of the active ingredient by cells via endocytosis[14, 18] (such uptake may play a role in the therapeutic effect). The diameter of liposomes used in the examples below was between 0.15 to 300 nm. However, this is non-limiting, but merely an example, and liposomes of other size ranges may also be used.

In addition, the active ingredient may be encapsulated or embedded in inert polymeric particles such as, for example, any of the microcapsules, nanocapsules, nanoparticles, nanospheres, microspheres, microparticles, etc. known in the art[19]. The release of the active ingredient from such particles may be a controlled release which results, in some cases, in prolonged and enhanced effect and uptake of said active ingredient.

The pharmaceutical carrier or diluent used in the composition of the invention may be any one of the conventional solid or liquid carriers known in the art. A solid carrier for example may be lactose, sucrose, talc, gelatin, agar, etc. Where the carrier is liquid carrier it may be for example peanut oil, phospholipids, water etc. Where the solid carrier is used for oral administration, the composition may be in the form of a tablet, in the form of a hard capsule (e.g. a gelatin capsule), in the form of powder or in pellet form. Where a liquid carrier is used, the preparation may be in the form of a syrup, emulsion, liposomes, soft gelatin capsule or sterile injectable liquid such as a liposome preparation, an aqueous or non-aqueous liquid suspension or a solution[17].

The composition of the invention used for injection may be selected from emulsions, solutions, suspensions, colloidal solutions containing suitable additives, etc.

The compositions of the invention may be administered by any route which effectively transports the active compound to the appropriate or desirable site of action. By a preferred embodiment of the invention the modes of administration are intravenous (i.v.) and intra-arterial (i.a.) (particularly suitable for on-line administration). Other modes of administration include intramuscular (i.m.) or subcutaneous (s.c.). Such administration may be bolus injections or infusions. The compositions may also be administered locally to the diseased site of the artery, for example, by means of a suitable oozing/sweating balloon known in the art. Another mode of administration may be by perivascular delivery, coating of the delivery system on a balloon or a stent or by any of the other methods of cardiovascular drug delivery systems known in the art. Combinations of any of the above routes of administration may also be used in accordance with the invention.

The dosage of the active ingredient to be used also depends on the specific activity of the used active ingredient, on the mode of administration (e.g., systemic administration or local delivery), the form of the active ingredient (e.g., whether it is in the form of a drug, in a form of a polymer, whether it is encapsulated in a particle such as a liposome, etc.), and other factors as known per se.

In accordance with a preferred embodiment of the invention, treatment of an individual with the active ingredient may be for the purpose of preventing restenosis before its occurrence. For prevention, the active ingredient may be administered to the individual before angioplasty procedure, during the procedure or after the procedure as well as combination of before, during and after procedural administration.

In accordance with another embodiment of the invention, the active ingredient is administered to an individual suffering from restenosis for the purpose of reducing or treating restenosis. In such a case, the active ingredient may also be administered to the individual at different periods of time after restenosis is discovered, either alone or in combination with other kinds of treatments.

In addition, the active ingredient may be administered before any other conditions which may yield accelerated arteriosclerosis, as well as acutely after the process has begun to inhibit further development of the condition.

BRIEF DESCRIPTION OF THE DRAWINGS

FIGS. 1–3 are bar graphs of results demonstrating the effect of Clodronate encapsulated in liposomes on the reduction of restenosis in an experimental rat carotid catheter injury model as compared to the effect of control liposomes which did not contain clodronate on the same rats. In these figures: carotid catheter injury model as compared to the effect of control liposomes which did not contain clodronate on the same rats. In these figures:

EXAMPLES

The invention will now be demonstrated by way of non limiting examples with reference to the accompanying drawings:

Example 1

Materials and Methods

Liposomes of Clodronate

Stock solutions of clodronate were prepared by dissolving the drug in deionized water at a concentration of 0.11 M, pH=7.

Liposome Preparation 38.9 mg of distearoylphosphatidylglycerol (DSPG), 118.5 mg of distearoylphosphatidylcholine (DSPC) and 38.7 mg of cholesterol were accurately weighed and dissolved in 20 ml of chloroform: methanol (9:1) in a round bottom vial. The vial was gently warmed. The solvent was then evaporated in rotavapor. 20 mls of hydrated diisopropylether were then added and the vial was put into a water bath until the contents were dissolved. 8 mls of the clodronate solution prepared as described above, were then added, and the solution was sonicated at 55 C for a period of 45 mins. The organic phase was then evaporated in rotavapor (55 C, 100 rpm). Similarly, other drug-containing liposomes can be prepared.

Purification of Prepared Liposomes

A Sephadex gel was prepared by dissolving 2.6 gr of Sephadex G-50 in 40 mls of water and stabilizing over night. The column was rinsed with 100 mls of buffer (50 mM Mes+50 mM HEPES+75 mM NaCl, pH 7.2). The liposomes were applied to the column and the column was rinsed with the buffer. The liposome is seen as a band which can be followed in the column by its color. About 20 drops were collected from the column into each tube.

Animals

Animals were obtained and housed in the animal facilities of the Faculty of Medicine, The Hebrew University of Jerusalem conforming to the standards for care and use of laboratory animals of the Hebrew University of Jerusalem. Male rats of Sabra strain weighing 350–420 g were used. The animals were fed standard laboratory chow and tap water ad libitum. All in vivo experiments were made under general anesthesia achieved with 80 mg/kg ketamine and 5 mg/kg xylazine administered i.p.

Rat Carotid Catheter Injury Model

The distal left common and external carotid arteries were exposed through a midline incision in the neck. The left common carotid artery was denuded of endothelium by the intraluminal passage of a 2F balloon catheter introduced through the external carotid artery. The catheter was passed three times with the balloon distended sufficiently with saline to generate a slight resistance. The catheter was then removed and the external carotid artery was ligated, and the wound was closed with surgical staples.

Seven rats served as the control group, and 6 rats as the treated group (randomly chosen). Liposomal clodronate was injected I.V. to the "treated group" one day prior to the arterial injury (6 mg of clodronate per rat) and repeated on day 6. In the control group similar injections were administered but with "empty" liposomes (no clodronate).

All animals were sacrificed 14 days after injury by an overdose of pentobarbital. Arteries were perfusion-fixed with 150ml of 4% formaldehyde solution pH 7.4 at 100 mm Hg. The right atrium was dissected and an 18G catheter connected to the perfusion system was inserted in the left ventricle. The arterial segments were dissected, cut, gently separated from the polymer, and postfixed for at least 48 hrs. in the same fixative solution. The arterial segments were embedded in paraffin and cut at 8–10 sites 600 $\mu$m apart, and sections of 6 $\mu$m were mounted and stained with Verhoeff's elastin stain for histologic examination.

Mormhometric Analysis

The slides were examined microscopically by an investigator blinded to the type of the experimental group. Six to 8 sections in each slide were evaluated by computerized morphometric analysis and the averaged section data were further used as a representative of a whole slide for comparisons between groups. The residual lumen, the area bounded by the internal elastic lamina (original lumen), and the area circumscribed by the external elastic lamina ("total arterial area") were measured directly. The degree of neointimal thickening was expressed as the ratio between the area of the neointima and the original lumen (% stenosis), and as the ratio between the neointimal area to the area of the media (N/M). The medial area, an indirect index of SMC viability, was determined as the difference between the total arterial area and the original lumen area.

Results

The surgical procedure and treatment did not cause mortality or apparent morbidity of the animals.

Figure 1A:
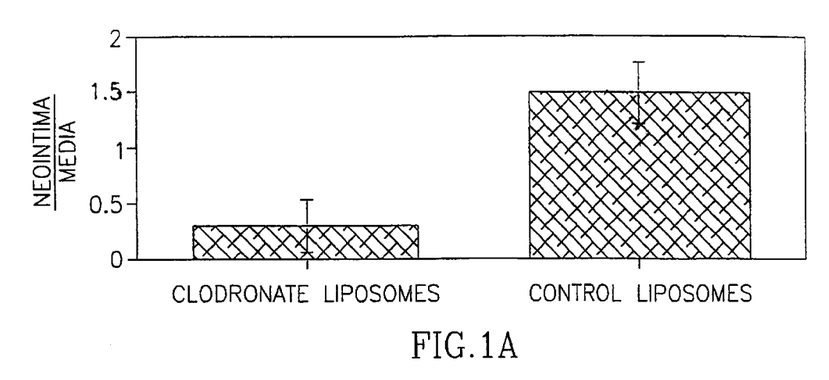
FIG. 1 shows the extent of mean luminal intimal formation and mean neointima to media ratio in rats treated with Clodronate containing liposomes as compared to rats treated with control liposomes.
Figure 2:
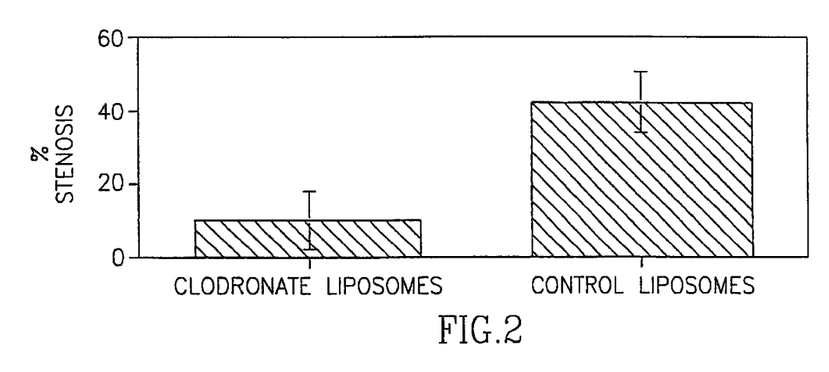
FIG. 2 shows the % stenosis in rats treated with Clodronate containing liposomes as compared to the % stenosis in rats treated with control liposomes.
Figure 3:
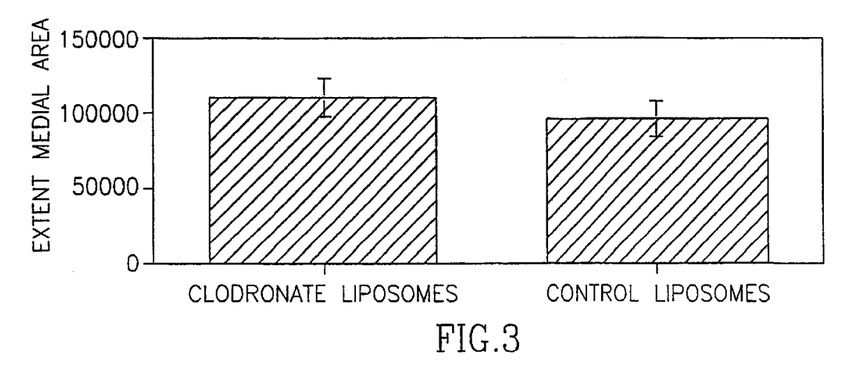
FIG. 3 shows the extent of medial area as an indirect index of smooth muscle cell viability and determined as the difference between the total arterial area and the original lumen area in rats treated with Clodronate containing liposomes as compared to rats treated with control liposomes only.

As seen in FIG. 1 the extent of mean neointimal formation and mean neointima to media ratio (N/M) following treatment with clodronate-encapsulated in liposomes was significantly reduced. The N/M ratio in clodronate treated rats was 0.28±0.23 as compared to 1.42±0.26 in the control group (mean±SD, p<0.01). Similarly as seen in FIG. 2, significant inhibition of % stenosis was achieved in the treated group: 9.8±7.76 vs. 41.53±7.9, treated and control groups, respectively (mean±SD, p<0.01). There were no apparent systemic side effects nor any effects on somatic growth as seen in FIG. 3.

Conclusion: Treatment of rats with clodronate-containing liposomes significantly reduces restenosis seen as neointimal formation following balloon-injury of the carotid artery.

Example 2
Materials and Methods

The antirestenotic effects of liposomal clodronate injections were studied in the balloon-injured rat and atherosclerotic rabbit carotid arterial models. The rats were treated by clodronate-containing liposomes, empty liposomes (control), and clodronate in solution (additional control). The dose of clodronate injected was 1.5 and 15 mg/kg administered one day before procedure (−1) and/or on day 6 (+6) post injury. The rabbits (following 30 days of atherosclerotic diet) were treated one day prior to balloon angioplasty by liposomal clodronate (10 mg/kg). The lumen, neointimal, medial and vessel areas and volumes were measured in the treated and control animal groups by digital planimetry of histological sections, at 14 and 30 days post injury in the rat and rabbit models, respectively.

Results

The results are shown in the following Table 1.

| Treatment type | Animal (No.) | Dosing days | N/M | % stenosis |
|---|---|---|---|---|
| Empty liposomes | Rat (20) | −1, +6 | 1.62 ± 0.1 | 44.5 ± 2.0 |
| Clodronate | Rat (10) | −1, +6 | 1.2 ± 0.2 | 40.2 ± 7.2 |
| Liposomal clodronate 15 mg/kg | Rat (10) | −1 | 0.45 ± 0.1 | 15.4 ± 3.4 |
| Liposomal clodronate 15 mg/kg | Rat (10) | −1, +6 | 0.35 ± 0.07 | 12.0 ± 2.3 |
| Empty liposomes | Rabbit (10) | −1 | 1.94 ± 0.3 | 86.6 ± 4.0 |
| Liposomal clodronate 10 mg/kg | Rabbit (10) | −1 | 1.11 ± 0.2 | 71.5 ± 2.1 |
| Silica particles 1000 mg/kg | Rat (10) | −1 | 0.8 ± 0.1 | 24.2 ± 3.8 |

As can be seen, no significant differences were found between treatments with empty liposomes, and free clodronate in solution (see table), exhibiting marked neointimal formation. The extent of mean neointimal formation, mean neointima to media ratio (N/M), and % stenosis following treatment with clodronate-laden liposomes was significantly reduced. The medial area was not affected by the various treatments, indicating no deleterious effects on quiescent cells. Moreover, there were neither apparent systemic side effects nor any effects on bone and somatic growth. Significantly more potent treatments, with no significant difference between them, were the 1×15 mg/kg (−1) and 2×15 mg/kg (−1, and +6) injections. Similar findings of no adverse effects were observed in the rabbits' study. Liposomal clondronate was significantly effective in reducing neointimal formation and % stenosis.

Injection of silica particles also reduces intimal formation (Table 1). This effect could be attributed to the known inhibiting effect of silica on macrophages.

The results show that treatment by clodronate-containing liposomes significantly reduces neointimal formation following balloon-injury in both rat and rabbit models. There were neither apparent systemic and local side effects nor any effects on somatic growth. It should be noted that although BP are known as affecting bone, no effects on the bone nor on calcium and phosphorus levels in bone and blood were observed, following treatment with liposomal preparation of clodronate.

What is claimed is:

1. A method of treating restenosis, comprising:

administering to an individual in need thereof an effective amount of a formulation comprising a bisphosphonate encapsulated in a liposome, wherein said formulation has a size range of 0.1–1.0 microns, thereby treating restenosis.

2. The method according to claim 1, wherein the administering is intravenous, intra-arteria, intramuscular or subcutaneous.

3. The method according to claim 1, wherein said bisphosphonate comprises a compound having the following formula (I):

wherein $R_1$ is H, OH or halogen group; and $R_2$ is halogen; linear or branched $C_1$–$C_{10}$ alkyl or $C_2$–$C_{10}$ alkenyl, optionally substituted by heteroaryl or heterocyclyl $C_1$–$C_{10}$ alkylamino or $C_3$–$C_8$ cycloalkylamino, where the amino may be a primary, secondary or tertiary amino; —NHY where Y is hydrogen, $C_3$–$C_8$ cycloalkyl, aryl or heteroaryl; or —SZ, where Z is chlorosubstituted phenyl or pyridinyl.

4. The method according to claim 1, wherein said bisphosphonate is selected from the group consisting of clodronate, etidronate, tiludronate, pamidronate, and alendronate.

5. The method according to claim 1 or 4, wherein said individual is one having coronary restenosis.

6. The method according to claim 1 or 2, wherein the formulation is administered systemically.

* * * * *

UNITED STATES PATENT AND TRADEMARK OFFICE
CERTIFICATE OF CORRECTION

PATENT NO. : 6,719,998 B1
DATED : April 13, 2004
INVENTOR(S) : Jukka Mönkkönen et al.

It is certified that error appears in the above-identified patent and that said Letters Patent is hereby corrected as shown below:

Title page,
Item [75], Inventors, insert the following: -- Jukka Mönkkönen and Ilia Fishbein. --

Column 2,
Line 56, "Cs-Cg" should read -- $C_3$-$C_8$ --.
Line 57, correct the spelling of "cycloalky" (first word).

Column 3,
Lines 37 and 45, correct the spelling of "restenosis."

Column 4,
Line 43, "(UC)" should read -- (IV) --.

Column 5,
Line 20, insert an indent for a paragraph before "The BPs belonging to."

Column 6,
Line 9, "phosphatidylcholine" should read -- phosphatidyl-choline --.

Column 7,
Lines 50 and 51, "distearoylphosphatidyglycerol" should read -- distearoylphosphatidy-glycerol --

Column 10,
Line 19, "intra-arteria," should read -- intra-arterial, --.
Line 37, "amino" should read -- amine --.

Signed and Sealed this

Fourteenth Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,719,998 B1
DATED : April 13, 2004
INVENTOR(S) : Jukka Mönkkönen et al.

It is certified that error appears in the above-identified patent and that said Letters Patent is hereby corrected as shown below:

Title page,
Item [75], Inventors, insert the following:
-- Jukka Mönkkönen and Llia Fishbein --

Column 2,
Line 56, "Cs-Cg" should read -- $C_3$-$C_8$ --.
Line 57, correct the spelling of "cycloalky" (first word).

Column 3,
Lines 37 and 45, correct the spelling of "restenosis."

Column 4,
Line 43, "(UC)" should read -- (IV) --.

Column 5,
Line 20, insert an indent for a paragraph before "The BPs belonging to."

Column 6,
Line 9, "phosphatidylcholine" should read -- phosphatidyl-choline --.

Column 7,
Lines 50-51, "distearoylphosphatidyglycerol" should read -- distearoylphosphatidy-glycerol --.

UNITED STATES PATENT AND TRADEMARK OFFICE
CERTIFICATE OF CORRECTION

PATENT NO. : 6,719,998 B1
DATED : April 13, 2004
INVENTOR(S) : Jukka Mönkkönen et al.

It is certified that error appears in the above-identified patent and that said Letters Patent is hereby corrected as shown below:

Column 10,
Line 19, "intra-arteria," should read -- intra-arterial, --.
Line 37, "amino" should read -- amine --.

Signed and Sealed this

Eighteenth Day of January, 2005

JON W. DUDAS
*Director of the United States Patent and Trademark Office*